US005468892A

United States Patent [19]
de Riese-Meyer et al.

[11] Patent Number: 5,468,892
[45] Date of Patent: Nov. 21, 1995

[54] PROCESS FOR THE PRODUCTION OF AN ALUMINUM TRIFORMATE SOLUTION CONTAINING ALKALI METAL AND/OR ALKALINE EARTH METAL, HIGHLY CONCENTRATED ALUMINUM TRIFORMATE SOLUTIONS CONTAINING ALKALI AND/OR ALKALINE EARTH METAL, AND THEIR USE

[75] Inventors: Loert de Riese-Meyer; Rudolf Zauns-Huber, both of Duesseldorf, Germany

[73] Assignee: Henkel Kommanditgesellechaft auf Aktien, Duesseldorf, Germany

[21] Appl. No.: 167,837

[22] Filed: Dec. 20, 1993

[51] Int. Cl.$^6$ .................................................. C07F 5/06
[52] U.S. Cl. ........................................ 556/171; 556/183
[58] Field of Search ...................... 556/171, 183

[56] References Cited

U.S. PATENT DOCUMENTS

| | | | |
|---|---|---|---|
| 2,289,286 | 7/1942 | Mazabraud | 260/448 |
| 4,278,610 | 7/1981 | Maurer et al. | 260/438.1 |
| 4,601,340 | 7/1986 | Fodor et al. | 166/294 |

FOREIGN PATENT DOCUMENTS 2325018 12/1973 Germany.

OTHER PUBLICATIONS

Chaplygina, *Zh. Neorg. Khim.*, 32(2), pp. 484–486 (1987). CA106: 126750v (1987).
Kirk Othmar, Enzyklopaedie of Chemical Technology, 3. Auflage, Band 2, S. 204, (1978).

*Primary Examiner*—José G. Dees
*Assistant Examiner*—Barbara S. Frazier
*Attorney, Agent, or Firm*—Wayne C. Jaeschke; Norvell E. Wisdom, Jr.; Daniel S. Ortiz

[57] ABSTRACT

The invention concerns a method of preparing preferably highly concentrated aluminum triformate solutions containing alkali metals and/or alkaline earth metals, by the neutralization of an alkaline aluminate solution containing alkali metals and/or alkaline earth metals by adding formic acid, and subsequently heating the solid precipitated to give a clear, stable aluminum triformate solution. The invention also concerns highly concentrated aluminum triformate solutions containing alkali metals and/or alkaline earth metals and the use of such solutions to impregnate textiles, in disinfectant and cleaning agents, as a coagulant for paints, or as a setting agent in leather processing.

20 Claims, No Drawings

PROCESS FOR THE PRODUCTION OF AN ALUMINUM TRIFORMATE SOLUTION CONTAINING ALKALI METAL AND/OR ALKALINE EARTH METAL, HIGHLY CONCENTRATED ALUMINUM TRIFORMATE SOLUTIONS CONTAINING ALKALI AND/OR ALKALINE EARTH METAL, AND THEIR USE

This application is a 371 of PCT EP91/01139, filed on Jun. 20, 1991.

FIELD OF THE INVENTION

This invention relates to a process for the production of an aluminum triformate solution containing alkali metal and/or alkaline earth metal, by neutralization of an aluminate liquor with a solution containing formic acid introduced beforehand, to the resulting highly concentrated aluminum triformate solutions containing alkali metal and/or alkaline earth metal, and to their use for impregnating textiles, in disinfectants and cleaning products, as coagulants for lacquers, or as fixing agents in the processing of leather.

STATEMENT OF RELATED ART

It is known from the prior art that aqueous aluminum triformate solutions can be obtained either by reaction of freshly precipitated aluminum hydroxide with formic acid or by the reaction of barium formate with aluminum sulfate in water (see *Ullmann*, Vol. 3, page 448, 1953). However, the disadvantages of this process lie on the one hand in the ageing of aluminum hydroxides, which is troublesome for technical purposes, and, on the other hand, in the barium formate which makes the process unprofitable because of its high price. The reaction of formic acid with other reactive aluminum compounds, such as aluminum halides or aluminum hydroxychloride, has the disadvantage that the product is additionally burdened by halide.

DE-A-23 25 018 describes an electrochemical process for the production of aluminum triformate solutions in which aluminum is electrochemically dissolved in formic acid. However, this process must be regarded as extremely expensive from the point of view of the equipment required.

In addition, it is known that the production of highly concentrated aluminum triformate solutions is problematical. Thus, solid aluminum triformate, for example, is only sparingly soluble in cold water and, even in boiling water, only forms an about 25% by weight aqueous solution (see Kirk-Othmer, *Encyclopedia of Chemical Technology*, 3rd Edition, Vol. 2, page 204, 1978). Another disadvantage of these supersaturated hot aluminum triformate solutions is that some of the aluminum triformate crystallizes out again on cooling. In view of the difficulties involved in the production of highly concentrated aluminum triformate solutions, aluminum triformate is only marketed as a solid or as basic aluminum formates with a considerable content of free hydroxyl groups. However, highly concentrated solutions are desirable for applicational reasons, such as handling and dispensing.

DESCRIPTION OF THE INVENTION

1. Object of the Invention

Now, the problem addressed by the present invention was to provide a process for the production of aluminum triformate solutions which would not involve the use of corrosion-promoting halides, would start out from readily available and inexpensive raw materials and would lead to highly concentrated solutions with good handling and dispensing properties.

2. Summary of the Invention

Accordingly, the present invention is to a process for the production of an aluminum triformate solution containing alkali metal and/or alkaline earth metal from an aluminate liquor using formic acid, characterized in that an aqueous aluminate liquor containing alkali metal and/or alkaline earth metal is neutralized with a formic acid introduced beforehand and the solid precipitated is converted by heating into a clear aluminum triformate solution.

The advantages of the process according to the invention lie on the one hand in the high concentration and stability of the resulting aluminum triformate solutions containing alkali metal and/or alkaline earth metal and, on the other hand, in the low raw material and production costs of the aluminate liquor, because the aluminate liquor is also used, for example, in the production of zeolites. Although the present invention is mainly concerned with the production of highly concentrated aluminum triformate solutions, aluminum triformate solutions of relatively low concentration may also be produced, if desired, by the process according to the invention. To this end, the concentrations in which the starting materials are used will be adapted to the desired final concentration of the aluminum triformate solution and the reaction conditions will be selected accordingly, as described hereinafter. Accordingly, the process according to the invention may be used both for the production of highly concentrated aluminum triformate solutions and for the production of relatively low-concentration aluminum formate solutions.

DESCRIPTION OF PREFERRED EMBODIMENTS

In the context of the invention, aluminate liquor is understood to be an aqueous solution of a mixture of aluminum oxide and/or hydroxide and alkali metal and/or alkaline earth metal oxides and/or hydroxides, preferably sodium oxide and/or hydroxide, with an aluminum content of 10 to 350 g/l and preferably 70 to 200 g/l and an alkali metal or alkaline earth metal content, preferably a sodium content, of 10 to 350 g/l and, more preferably, 130 to 220 g/l.

According to the invention, the aluminate liquors may in principle contain any oxides and/or hydroxides of alkali and alkaline earth metals. However, the oxides and/or hydroxides of sodium, potassium, calcium, magnesium and/or barium are particularly preferred. Traces of iron oxide occasionally present generally lead to a slight yellow coloration of the aluminum triformate solutions, although this does not particularly affect their useability.

In one preferred embodiment of the invention, an aqueous sodium aluminate liquor with a ratio by weight of sodium oxide to aluminum oxide of 5:1 to 1:5 and preferably 2:1 to 1:2 is used for the production of a sodium-containing aluminum triformate solution. In commercially obtainable sodium aluminate liquors, the ratio by weight of sodium oxide to aluminum oxide is generally of the order of 0.5 to 1.5:1 for reasons of stability because, if the sodium hydroxide content is too low, aluminum trihydroxide can precipitate. The aqueous sodium aluminate liquors may contain various other alkali and/or alkaline earth metal cations as impurities, depending on their origin. In this way, potassium or barium cations, for example, may be introduced into the aqueous sodium aluminate liquor and hence into the aluminum triformate solution in the form of their monoformates or diformates in quantities of up to a few percent by weight.

In the process according to the invention, the sodium aluminate liquor is neutralized at an aluminum content of 10 to 80 g/l without external cooling at temperatures of 5° to 110° C. and preferably at temperatures of 25° to 80° C., using the heat of neutralization. By contrast, at an aluminum content of 80 to 350 g/l and preferably 80 to 220 g/l, temperatures below 25° C. and preferably below 15° C. have to be used. In principle, temperatures from the freezing point of the particular solution used to below 25° C. and preferably to below 15° C. may be applied. However, in view of the melting point of the particular formic acid used, which is 8.4° C. for 100% formic acid and 13.8° C. for 85% aqueous formic acid, appropriate external cooling will be used, particularly at excessive aluminum contents.

This preference according to the invention for relatively low reaction temperatures with increasing aluminum content in the sodium aluminate liquor is attributable to the fact that the heat of neutralization can lead to reaction temperatures above 80° C. if the aluminum content is too high. At temperatures of this order, the aluminum is partly precipitated in the form of aluminum oxide, so that highly concentrated aluminum triformate solutions cannot be produced.

According to the invention, a pure 100% formic acid or mixtures with water, preferably an 80 to 99% by weight aqueous formic acid solution, may be used as the formic acid.

In one general embodiment of the invention, the neutralization of the aluminate liquor containing alkali metal and/or alkaline earth metal with the formic acid is carried out by initially introducing the formic acid to establish an acidic pH value and then introducing the aluminate liquor either continuously or discontinuously. In one preferred embodiment, the neutralization of the highly alkaline aluminate liquor with the formic acid introduced beforehand is carried out from an initial pH value of approximately 0 to 2 to a pH value of at most 4.5 and, preferably, to a pH value of at most 4. The limitation of the pH value of the neutralization reaction in accordance with the present invention may readily be explained by the precipitation of aluminum trihydroxide and basic aluminum formate at relatively high alkaline pH values. In principle, therefore, neutralization may even be continued to neutral or alkaline pH values, although in this case losses of concentration have to be accepted.

According to the invention, the molar ratio of aluminum to formic acid is 1:1 to 1:10 and preferably 1:2.5 to 1:3.5. To guarantee a stoichiometric reaction, a molar ratio of aluminum to formic acid of 1:3 is particularly preferred. In stating the molar ratio of aluminum to formic acid, however, it is important to bear in mind that the cations containing alkali metal and/or alkaline earth metal will also consume formic acid. For this reason, the formic acid is generally used in an excess over and above the molar ratios mentioned above, the excess being selected in accordance with the percentage content of other cations in the reaction mixture, i.e. alkali metal and/or alkaline earth metal ions.

In general, a gel-like white solid accumulates during the neutralization reaction according to the invention and has to be redissolved in a following heating step. To produce a clear highly concentrated aluminum triformate solution in accordance with the invention, the white solid is intensively stirred at a temperature of 25° to 110° C. and preferably at a temperature of 50° to 80° C. until a clear solution is obtained. In general, a period of 5 to 60 minutes is sufficient to dissolve the solid and to obtain a clear stable solution.

According to the invention, the neutralization step may even be preceded and/or followed by the use of stabilizers, such as preferably ethylenediamine tetraacetic acid, sulfophthalic acid, sulfosalicylic acid or the water-soluble salts of these acids, more particularly their alkali metal salts, the corresponding sodium salts being particularly preferred, and/or isopropanol which, if desired, may be used in admixture with organic solvents, such as alcohols or other readily water-miscible solvents, and/or water. The particular concentrations of stabilizer, which are generally in the range from 0.1 to 10% by weight and preferably in the range from 0.5 to 2% by weight, must be varied by one skilled in the art to meet particular requirements. For example, the addition of stabilizers may be entirely appropriate for increasing the stability of the aluminum triformate solutions in storage, optionally at relatively low temperatures. In this case, the quantity of stabilizer added is governed by the concentration of the particular aluminum triformate solution, i.e., the higher the concentration of the aluminum triformate solution, the larger the quantity in which the stabilizer is added.

The present invention also relates to the highly concentrated aluminum triformate solutions containing alkali metal and/or alkaline earth metal produced by the process according to the invention, which contain 1 to 50% by weight and preferably 5 to 30% by weight of alkali and/or alkaline earth metal formate and 25 to 50% by weight and preferably 30 to 40% by weight of aluminum triformate. These highly concentrated aluminum triformate solutions containing alkali metal and/or alkaline earth metal are obtained in particular when a high aluminum content is coupled with low temperatures.

Potential applications for the highly concentrated aluminum triformate solutions are, in particular, the applications known from the prior art in which a troublesome content of alkali and/or alkaline earth metal formates has no effect.

The present invention also relates to the use of the highly concentrated aluminum triformate solutions containing alkali metal and/or alkaline earth metal according to the invention in the impregnation of textiles, in disinfectants and cleaning products, as coagulants for lacquers, or as fixing agents in the processing of leather. In addition, the aluminum triformate solutions according to the invention may be used in the sizing of paper, in the silaging of green fodder, or as a mordant in the textile and tobacco industry.

EXAMPLES

EXAMPLE 1

2000 g of an aqueous sodium aluminate liquor containing 14.3% by weight of sodium oxide and 11.6% by weight of aluminum oxide were added dropwise over a period of 20 minutes at room temperature to 1030 g of formic acid (100%). An increase in temperature up to 80° C. and precipitation occurred. The mixture was then heated under reflux for about 15 to 30 minutes until a clear solution was obtained. The yellow solution contained about 24.3% by weight of aluminum triformate and 20.7% by weight of sodium formate at a pH value of 3.9.

EXAMPLE 2

2000 g of an aqueous sodium aluminate liquor containing 14.3% by weight of sodium oxide and 11.6% by weight of aluminum oxide were added dropwise over a period of 20 minutes at room temperature to 1210 g of an 85% aqueous formic acid. An increase in temperature up to 80° C. and precipitation occurred. The mixture was then heated under reflux for about 15 to 30 minutes until a clear solution was obtained. The yellow solution contained about 23% by weight of aluminum triformate and 19.5% by weight of sodium formate at a pH value of 3.9.

EXAMPLE 3

2000 g of an aqueous DYNAFLOC L solution (a product of Dynamit Nobel, 19% by weight sodium oxide and 25% by weight aluminum oxide) was added dropwise with vigorous stirring and external cooling with cold water to 2260 g of an 85% aqueous formic acid. The dropwise addition rate was governed by the temperature of the reaction solution, which should not exceed 15° C. After about 45 minutes, the mixture was stirred at 60° C. until a clear solution was obtained. The colorless solution contained about 37.3% by weight of aluminum triformate and 19.6% by weight of sodium formate at a pH value of 3.5.

EXAMPLE 4

2000 g of an aqueous DYNAFLOC L solution (a product of Dynamit Nobel, 19% by weight $Na_2O$, 25% by weight $Al_2O_3$) were added dropwise with vigorous stirring and external cooling with cold water to 1920 g of formic acid (100%). The dropwise addition rate was governed by the temperature of the reaction solution, which should not exceed 15° C. (duration about 45 minutes). The mixture was then stirred at 60° C. until a clear solution was obtained (about 10 minutes). The colorless solution contained 40.5% by weight of aluminum triformate and 21.3% by weight of sodium formate at a pH value of 3.7.

EXAMPLE 5

2000 g of an aqueous DYNAFLOC L solution (a product of Dynamit Nobel, 15.3% by weight $Na_2O$, 20.2% by weight $Al_2O_3$) were added dropwise with vigorous and external cooling with cold water to 2260 g of an 85% aqueous formic acid. The dropwise addition rate was governed by the temperature of the reaction solution, which should not exceed 25° C. (duration about 20 minutes). The mixture was then stirred at 60° C. until a clear solution was obtained (about 10 minutes). The colorless solution contained 30.1% by weight of aluminum triformate and 15.8% by weight of sodium formate at a pH value of 3.7.

The invention claimed is:

1. A process for the production of a solution comprising aluminum triformate by neutralization of an aqueous aluminate liquor containing aluminum and at least one member selected from the group consisting of alkali metal and alkaline earth metal which comprises: neutralizing the aluminate liquor by introducing the aluminate liquor into formic acid the neutralization being carried out;

i) at a temperature of 5° C. to 110° C. when the aluminum content is from 10 to 80 g/l; or ii) at a temperature below 25° C. when the aluminum content is from above 80 to 350 g/l, to form a neutralized mixture containing a precipitated solid, and heating the neutralized mixture containing the precipitate to form a clear aluminum triformate solution.

2. A process of claim 1 wherein the aluminate liquor is an aqueous solution with an aluminum content of 70 to 200 g/l and a sodium content of 130 to 220 g/l.

3. A process as claimed in claim 2, wherein the aluminate liquor is an aqueous sodium aluminate liquor with a ratio by weight of sodium oxide to aluminum oxide of 5:1 to 1:5 and preferably 2:1 to 1:2.

4. A process as claimed in claim 3, wherein neutralization of the aluminate liquor is carried out to a pH value of at most 4.

5. A process as claimed in claim 4, wherein neutralization of the aluminate liquor is carried out with a molar ratio of aluminum to formic acid of 1:2.5 to 1:3.5.

6. A process as claimed in claim 5, wherein the solid precipitated after neutralization is converted into a clear solution with stirring at a temperature of 50° to 80° C.

7. A process as claimed in claim 6, wherein stabilizers selected from the group consisting of ethylenediamine tetraacetic acid, sulfophthalic acid, sulfosalicylic acid, water-soluble salts of these acids, and isopropanol, optionally in admixture with organic solvents or water, are used before, after, or both before and after neutralization.

8. A process as claimed in claim 1, wherein an aqueous solution of a mixture of aluminum oxide, hydroxide, or both oxide and hydroxide and alkali metal, alkaline earth metal, or both alkali metal and alkaline earth metal oxides, hydroxides, or both oxides and hydroxides with an aluminum content of 10 to 350 g/l and an alkali metal, alkaline earth metal, or both alkali metal and alkaline earth metal content of 10 to 350 g/l is used as the aluminate liquor.

9. A process as claimed in claim 8, wherein the aluminate liquor is an aqueous sodium aluminate liquor with a ratio by weight of sodium oxide to aluminum oxide of 5:1 to 1:5.

10. A process as claimed in claim 9, where the ratio by weight of sodium oxide to aluminum oxide is from 2:1 to 1:2.

11. A process as claimed in claim 1, wherein the aluminate liquor is an aqueous sodium aluminate liquor with a ratio by weight of sodium oxide to aluminum oxide of 5:1 to 1:5.

12. A process as claimed in claim 11, where the ratio by weight of sodium oxide to aluminum oxide is from 2:1 to 1:2.

13. A process as claimed in claim 2, wherein neutralization of the aluminate liquor is carried out to a pH value of at most 4.

14. A process as claimed in claim 1, wherein neutralization of the aluminate liquor is carried out to a pH value of at most 4.5.

15. A process as claimed in claim 1, wherein neutralization of the aluminate liquor is carried out with a molar ratio of aluminum to formic acid of 1:1 to 1:10.

16. A process as claimed in claim 4, wherein the solid precipitated after neutralization is converted into a clear solution with stirring at a temperature of 50° to 80° C.

17. A process as claimed in claim 1, wherein the solid precipitated after neutralization is converted into a clear solution with stirring at a temperature of 25° to 110° C.

18. A process as claimed in claim 1, wherein stabilizers, optionally in admixture with organic solvents or water, are used before, after, or both before and after neutralization.

19. Aluminum triformate solutions comprising an alkali metal, alkaline earth metal, or both alkali metal and alkaline earth metal formate content of 1 to 50% by weight and an aluminum triformate content of 25 to 50% by weight.

20. Aluminum triformate solutions as claimed in claim 19, comprising an alkali metal, alkaline each metal, or both alkali metal and alkaline each metal formate content of 5 to 30% by weight and an aluminum triformate content of 30 to 40% by weight.

* * * * *